United States Patent [19]

Yous et al.

[11] Patent Number: 5,420,158
[45] Date of Patent: May 30, 1995

[54] NAPHTHYLALKYLAMINES

[75] Inventors: Said Yous, Lille; Daniel Lesieur, Gondecourt; Patrick Depreux, Armentieres; Béatrice Guardiola-Lemaitre, Neuilly-Sur-Seine; Gérard Adam, Le Mesnil Le Roi; Pierre Renard, Versailles; Daniel H. Caignard, Paris, all of France

[73] Assignee: Adir et Compagnie, Courbevoie, France

[21] Appl. No.: 35,936

[22] Filed: Mar. 23, 1993

[30] Foreign Application Priority Data

Mar. 27, 1992 [FR] France .................. 92 03700

[51] Int. Cl.$^6$ .................. A01N 1/00; C07C 229/34
[52] U.S. Cl. .................. 514/510; 514/613; 514/657; 544/358; 544/106; 546/184; 548/579; 560/37; 560/38; 564/190; 564/191; 564/192
[58] Field of Search .................. 560/37, 38; 564/190, 564/191, 192; 548/579; 544/106, 358; 546/184; 514/510, 613, 657

[56] References Cited

U.S. PATENT DOCUMENTS 5,225,442  7/1993  Andrieux et al. .................. 564/190

OTHER PUBLICATIONS

Beaumont, et al., *J. Chem. Res. Synop.* (10) 332 (1979) (Search Report supplied).
Kessar et al., *J. Chem. Soc., C.* (2) 266–9 (1971).
Foltz, *J. Org. Chem.* 36(1) 24–7 (1971).
Young, et al. *J. Org. Chem.* 53(5) 1114–16 (1988).
Kazuoko Ota. Yakugaku Za 85(1) 14–20 (1965) [CA62:14590f].

*Primary Examiner*—José G. Dees
*Assistant Examiner*—Joseph M. Conrad, III
*Attorney, Agent, or Firm*—Gordon W. Hueschen

[57] ABSTRACT

The invention relates to a compound selected from those of general formula (I):

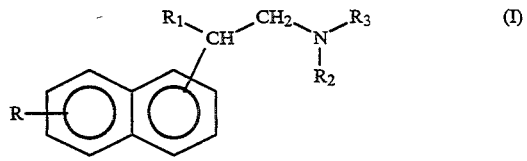

in which R, $R_1$, $R_2$ and $R_3$ are as defined in the specification, an optical isomer, and an addition salt thereof with a pharmaceutically-acceptable base.

Medicinal product which is useful in the treatment of disorders linked to abnormal melatonin activity.

18 Claims, No Drawings

NAPHTHYLALKYLAMINES

The invention relates to new naphthylalkylamines, to a process for preparing them and to pharmaceutical compositions containing them.

1-[2-(Acetylamino)ethyl]naphthalene, used in the synthesis of 1-[2-(phenylsulfonamido)ethyl]naphthalene compounds presented as thromboxane antagonists (DE 3,828,566), and N-[2-(1-naphthyl)ethyl]-4-bromobutyramide, described as a synthesis intermediate in Journal of Heterocyclic Chemistry vol. 2 (4), pp 378–384 (1965) are known in the literature.

Naphthylalkylamides of formula (a), claimed in Application EP 447,285,

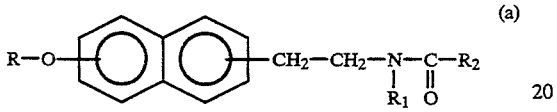

are also known from the prior art, as melatonin receptor agonists.

In the last ten years, many studies have demonstrated the major role of melatonin (5-methoxy-N-acetyltryptamine) in the control of the circadian rhythm and the endocrine functions, and the melatonin receptors have been characterized and localized.

In point of fact, the Applicant has now discovered new naphthylalkylamines showing a very high affinity for melatoninergic receptors and surprisingly possessing, in vitro and in vivo, very potent melatonin receptor-antagonist properties, which are hence opposite to those of the compounds of Application EP 447,285.

More specifically, the invention relates to the compounds of general formula (I):

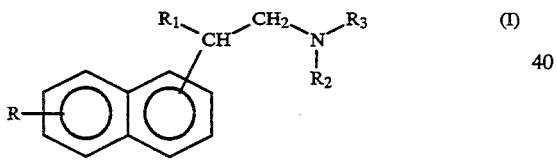

in which:
R represents a hydrogen atom or a group —O—$R_4$ in which $R_4$ denotes a hydrogen atom or a substituted or unsubstituted group chosen from alkyl, cycloalkyl, cycloalkylalkyl, phenyl, phenylalkyl and diphenylalkyl, $R_1$ represents a hydrogen atom or a group —CO—O—$R_5$ in which $R_5$ denotes a hydrogen atom or a substituted or unsubstituted alkyl group, $R_2$ represents a hydrogen atom or a group —$R'_2$ with $R'_2$ representing an alkyl or substituted alkyl radical, $R_3$ represents:
a group

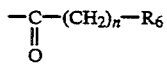

in which n represents 0 or an integer from 1 to 3 and $R_6$ represents a hydrogen atom or an alkyl, substituted alkyl, alkene, substituted alkene, cycloalkyl or substituted cycloalkyl group, or a substituted or unsubstituted heterocyclic group chosen from pyrrolidine, piperidine, piperazine, homopiperidine, homopiperazine, morpholine and thiomorpholine;

a group

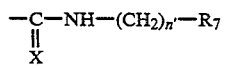

in which X represents an oxygen or sulfur atom, n' represents 0 or an integer from 1 to 3 and $R_7$ represents an alkyl, substituted alkyl, cycloalkyl, substituted cycloalkyl, phenyl or substituted phenyl group, on the understanding that if:
R represents an alkoxy group,
R represents a hydrogen atom and $R_3$ represents a group —CO—$R_8$ in which $R_8$ represents a hydrogen atom, a methyl group or a methyl or propyl group substituted with a halogen,
or if $R_3$ represents a group

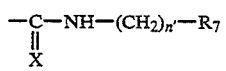

in which X, n' and $R_7$ are as defined above, then $R_1$ cannot be a hydrogen atom, their optical isomers and their addition salts with a pharmaceutically acceptable base, on the understanding that, except where otherwise specified, the term "substituted" means that the groups to which it relates may be substituted with one or more radicals chosen from halogen, ($C_1$–$C_4$) alkyl, ($C_1$–$C_4$) alkoxy, phenyl and phenylalkyl, it being possible for the phenyl rings themselves to be substituted with one or more halogen, ($C_1$–$C_4$) alkyl, ($C_1$–$C_4$) alkoxy, hydroxyl or trifluoromethyl radicals, the term "alkyl" denotes a group containing from 1 to 6 carbon atoms in an unbranched or branched chain, the term "alkene" denotes a group containing from 2 to 6 carbon atoms in an unbranched or branched chain, the term "cycloalkyl" denotes a saturated or unsaturated, mono- or bicyclic group containing from 3 to 10 carbon atoms.

Among pharmaceutically acceptable bases which can be used to form an addition salt with the compounds of the invention, there may be mentioned, as examples and without implied limitation, sodium hydroxide, potassium hydroxide, calcium hydroxide or aluminum hydroxide, alkali metal or alkaline earth metal carbonates and organic bases such as triethylamine, benzylamine, diethanolamine, tert-butylamine, dicyclohexylamine and arginine.

The invention also extends to the process for preparing the compounds of formula (I), wherein: a compound of formula (II):

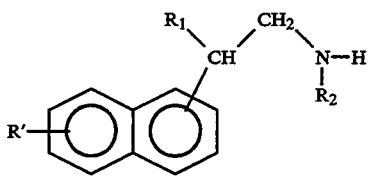 (II)

in which $R_1$ and $R_2$ are as defined in the formula (I) and R' represents a hydrogen atom, a hydroxyl group or an alkoxy group, is either reacted with an acid halide of formula (III):

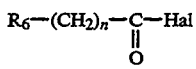 (III)

in which $R_6$ and n are as defined in the formula (I) and Hal represents a halogen atom, or with a compound of formula (III/a) during a catalytic hydrogenation

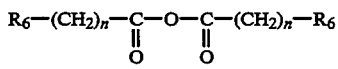 (III/a)

in which $R_6$ and n are as defined above, to obtain a compound of formula (I/a):

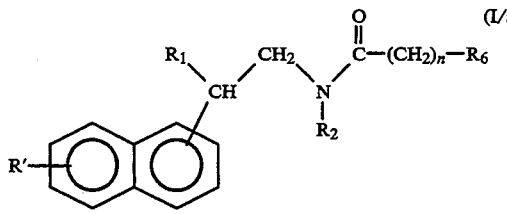 (I/a)

in which R', $R_1$, $R_2$, $R_6$ and n are as defined above, a special case of the compounds of formula (I) in which R represents a group R' and $R_3$ represents a group:

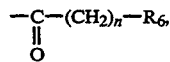

or reacted with an isocyanate or an isothiocyanate of formula (IV):

$$X=C=N-(CH_2)n'-R_7 \quad (IV)$$

in which X, n' and $R_7$ are as defined in the formula (I), to obtain a compound of formula (I/c):

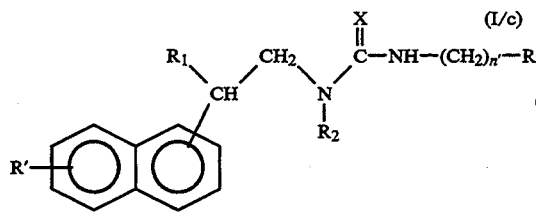 (I/c)

in which R', $R_1$, $R_2$, $R_7$, X and n' are as defined above, a special case of the compounds of formula (I) in which R represents a group R' and $R_3$ represents a group

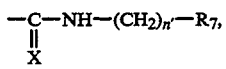

which compounds of formulae (I/a), (I/b) and (I/c) can also, when R' represents a hydroxyl group, be reacted with a compound of formula (V):

$$R''-Hal' \quad (V)$$

in which R" represents an unsubstituted or substituted group (the term substituted being as defined in the formula I) chosen from cycloalkyl, cycloalkylalkyl, phenyl, phenylalkyl and diphenylalkyl and Hal' represents a halogen atom, so as to obtain a compound of formula (I/d):

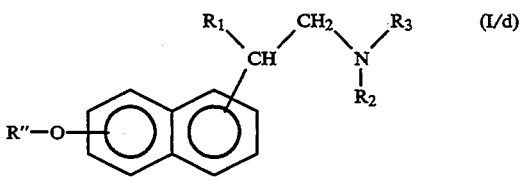 (I/d)

in which $R_1$, $R_2$, $R_3$ and R" are as defined above, a special case of the compounds of formula (I) in which R represents a group —O—R", the compounds of formulae (I/a), (I/b), (I/c) and (I/d) form collectively the compounds of formula (I), which compounds of formula (I) can, if so desired, be

- purified according to one or more purification methods chosen from crystallization, chromatography on silica gel, extraction, filtration and passage through charcoal or resin,
- separated, where appropriate, in pure form or in the form of a mixture, into their possible optical isomers,
- or salified, in the case where $R_1$ represents a carboxyl group or in the case where R represents a hydroxyl group, with a pharmaceutically acceptable base.

The invention also extends to the process for obtaining the compounds of formula (I/e):

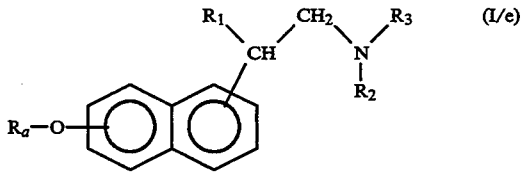 (I/e)

in which $R_1$, $R_2$ and $R_3$ are as defined in the formula (I) and $R_a$ represents a saturated cycloalkyl or cycloalkylalkyl group, a special case of the compounds of formula (I) in which R represents a group —O—$R_a$, wherein a compound of formula (I/f):

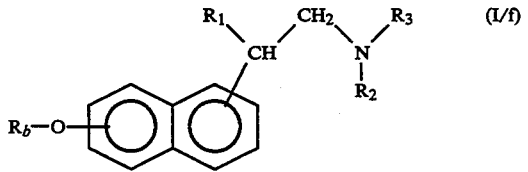 (I/f)

in which $R_1$, $R_2$ and $R_3$ are as defined above and $R_b$ represents an unsaturated cycloalkenyl or cycloalkenylalkyl group, a special case of the compounds of formula (I) in which R represents a group —O—$R_b$, is subjected to a catalytic hydrogenation to obtain the compound of formula (I/a), where $R_a$ corresponds to the saturated form of the group $R_b$, it being possible for the compounds of formula (I/e) to be:

- purified according to one or more purification methods chosen from crystallization, chromatography on silica gel, extraction, filtration and passage through charcoal or resin,
- separated, where appropriate, in pure form or in the form of a mixture, into their possible optical isomers,
- or salified, in the case where $R_1$ represents a carboxyl group, with a pharmaceutically acceptable base.

The compounds of formula (II) are readily accessible to a person skilled in the art:

either, when $R_1$ represents a group —CO—O—$R_5$ where $R_5$ is as defined in the formula (I), by reaction of a compound of formula (b):

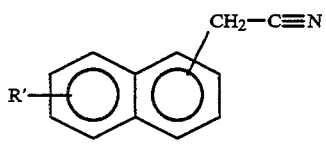

in which R' represents a hydrogen atom, a hydroxyl group or an alkoxy group, with a compound of formula (c):

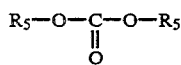

in which $R_5$ is as defined in the formula (I), to obtain a compound of formula (d):

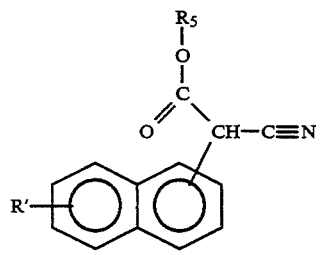

in which R' and $R_5$ are as defined above, which is then hydrogenated to obtain a compound of formula (II/a):

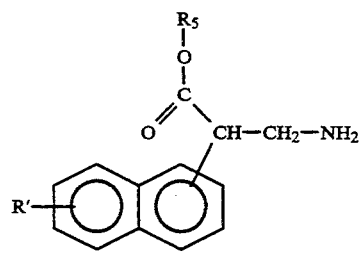

in which R' and $R_5$ are as defined above, which can then react with a compound of formula (e):

$$R'_2—Hal'' \qquad (e)$$

in which $R'_2$ is as defined in the formula (I) and Hal" represents a halogen atom, so as to obtain the compounds of formula (II/b):

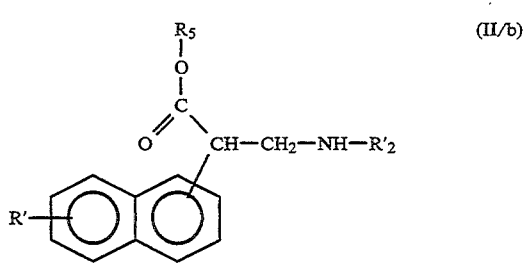

in which R', $R'_2$ and $R_5$ are as defined above, or, when $R_1$ represents a hydrogen atom, by reaction of the compounds of formula (II/c):

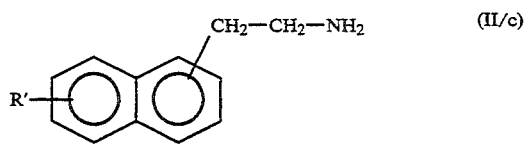

in which R' is as defined above, with a compound of formula (e) as defined above, to obtain compounds of formula (II/d):

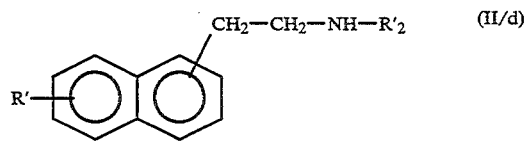

in which R' and $R'_2$ are as defined above, the compounds of formulae (II/a), (II/b), (II/c) and (II/d) forming collectively the compounds of formula (II), it being possible for the compounds of formulae (II/a), (II/b), (II/c) and (II/d), if so desired, to be purified, separated into their different isomers, or salified, where appropriate, with a base or an acid.

The starting materials used in the processes as described above are:

either commercially available, or readily accessible to a person skilled in the art according to processes described in the literature, and in particular in Application EP 447,285.

The compounds of formula (I) possess very advantageous pharmacological properties.

The Applicant discovered that the compounds of the invention possessed a high selective affinity for melatoninergic receptors and antagonized very strongly the action of melatonin.

This antagonist character of the compounds according to the invention is demonstrated in the pharmacological study (inhibition of cAMP synthesis in pars tuberalis cells, Example C, and inhibition of the activity of melatonin in the yenopus, Example D) of the present application, and proves surprising in the light of the opposite activity (that is to say melatonin receptor-agonist) of the closest compounds of the prior art, described in Application EP 447,285.

The compounds of the invention are hence capable of being used in the treatment of disorders linked to abnormal melatonin activity in the body.

It is apparent that the compounds of the invention may also be used for the treatment of disorders of the central nervous system, the immune system and the endocrine system.

The invention also extends to pharmaceutical compositions containing as active principle at least one of the compounds of formula (I) or one of its addition salts with a pharmaceutically acceptable base, in combination with one or more excipients, binding agents, flavoring agents, disintegrating agents, sweetening agents, lubricants or vehicles which are all suitable for pharmaceutical use.

Among the compositions according to the invention, there may be mentioned, as examples and without implying limitation, those which are suitable for oral, parenteral, ocular, per- or transcutaneous, nasal, rectal, perlingual or respiratory administration, and in particular injections, aerosols, eye or nose drops, tablets, sublingual tablets, capsules including hard gelatin capsules, troches, preparations to be absorbed from under the tongue, suppositories, creams, ointments and gels.

The preparations thereby obtained are generally presented in a form comprising measured doses, and can contain, depending on the pathology being treated and the patient's age and sex, from 0.01 to 10 mg in doses taken from one to three times a day.

The examples which follow illustrate the invention and in no way limit it.

EXAMPLE 1

N-[2-(1-naphthyl)ethyl]cyclobutanecarboxamide

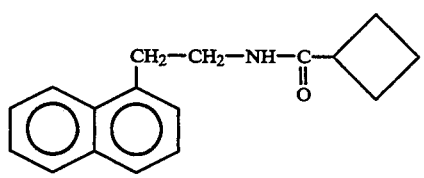

Exemple 1

0.01 mol of N-[2-(1-naphthyl)ethyl]amine hydrochloride is dissolved in a water/chloroform (40:60; vol/vol) mixture, and 0.02 mol of potassium carbonate is then added with magnetic stirring. The reaction mixture is cooled in an ice bath, and 0.01 mol of cyclobutanecarbonyl chloride is then added dropwise with magnetic stirring.

After stirring has been maintained for 30 minutes at room temperature, the chloroform phase is separated, washed with water and dried over calcium chloride, and the chloroform is then evaporated off under vacuum to obtain, after recrystallization of the residue in a toluene/cyclohexane mixture, N-[2-(1-naphthyl)ethyl]-cyclobutanecarboxamide.

Yield: 89% Melting point: 88°–89° C.
Elemental microanalysis:

|  | % C | % H | % N |
|---|---|---|---|
| calculated | 80.59 | 7,56 | 5.52 |
| found | 80.30 | 7.68 | 5.60 |

Spectral characteristics
Infrared: $\nu$ NH: 3280 cm$^{-1}$ $\nu$ CO: 1630 cm$^{-1}$
NMR (CDCl$_3$): 1.72–2.50 ppm; (unresolved complex, 6H); cyclobutyl CH$_2$ 2.68–3.04 ppm; (unresolved complex, 1H) ; cyclobutyl CH 3.28 ppm; (triplet, 2H); CH$_2$—CH$_2$—NH 3.60 ppm; (quintet, 2H ); CH$_2$—CH$_2$—NH 5.50 ppm; (signal, 1H); NH 7.28–8.20 ppm (unresolved complex, 7H); aromatic H

EXAMPLE 2

N-[2-(1-Naphthyl)Ethyl]Cyclopropanecarboxamide

By following the process of Example 1, replacing cyclobutanecarbonyl chloride by cyclopropanecarbonyl chloride, N-[2-(1-naphthyl)ethyl]cyclopropanecarboxamide is obtained. Recrystallization solvent: toluene/cyclohexane Yield: 88% Melting point: 117°–118° C.
Elemental microanalysis:

|  | % C | % H | % N |
|---|---|---|---|
| calculated | 80.30 | 7.16 | 5.85 |
| found | 80.24 | 6.89 | 5.87 |

Spectral characteristics
Infrared: $\nu$ NH: 3240 cm$^{-1}$ $\nu$ CO: 1630 cm$^{-1}$
NMR (CDCl$_3$): 0.50–1.40 ppm; (unresolved complex, 5H); cyclopropyl H 3.28 ppm; (triplet, 2H); CH$_2$—CH$_2$ NH 5.75 ppm; (signal, 1H); NH 7.3–8.2 ppm; (unresolved complex, 7H); aromatic H

EXAMPLE 3

N-[2-(1-naphthyl)ethyl]trifluoroacetamide

By following the process of Example 1, but replacing cyclobutanecarbonyl chloride by trifluoroacetyl chloride, N-[2-(1-naphthyl)ethyl]trifluoroacetamide is obtained.

Recrystallization solvent: cyclohexane
Yield: 89% Melting point: 79°–80° C.
Elemental microanalysis:

|  | % C | % H | % N |
|---|---|---|---|
| calculated | 80.59 | 7.56 | 5.52 |
| found | 80.30 | 7.68 | 5.60 |

Spectral characteristics
Infrared: $\nu$ NH: 3280 cm$^{-1}$ $\nu$ CO: 1630 cm$^{-1}$
NMR (CDCl$_3$): 3.30 ppm; (triplet, 2H); CH$_2$—CH$_2$—NH 3.72 ppm; (quintet, 2H); CH$_2$—CH$_2$—NH 6.50 ppm; (signal, 1H); NH 7.32–8.16 ppm; (unresolved complex, 7H) ; aromatic H

EXAMPLES 4 TO 10

Using the procedure described in Example 1, but replacing cyclobutanecarbonyl chloride by the appropriate acyl halide, the compounds of the following examples are successively obtained:

EXAMPLE 4

N-[2-(1-naphthyl)ethyl]propionamide

EXAMPLE 5

N-[2-(1-naphthyl)ethyl]isobutanecarboxamide

EXAMPLE 6

N-[2-(1-naphthyl)ethyl]cyclohexanecarboxamide

EXAMPLE 7

N-[2-(1-naphthyl)ethyl]-2-(1-piperazinyl)acetamide

EXAMPLE 8

N-[2-(1-naphthyl)ethyl]-2-(4-methyl-1-piperazinyl)acetamide

EXAMPLE 9

N-[2-(1-naphthyl)ethyl]-3-cyclopentylpropionamide

EXAMPLE 10

N-[2-(1-naphthyl)ethyl]butyramide

EXAMPLE 11

N-[2-(1-naphthyl)-2-(methoxycarbonyl)ethyl]cyclobutanecarboxamide

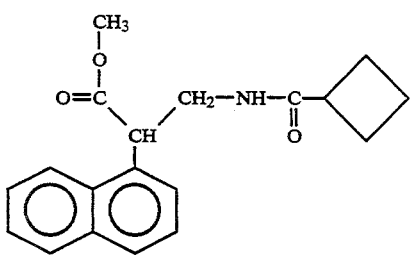

Exemple 11

Stage A:
2-(1-naphthyl)-2-(methoxycarbonyl)acetonitrile 0.1 mol of 2-(1-naphthyl)acetonitrile is dissolved in 120 cm³ of dimethyl carbonate, and the solution is heated to reflux. 0.1 mol of sodium is then added in small portions over 30 min, during which time the methanol evaporates off. The reaction medium is kept refluxing for 1 hour, and the excess dimethyl carbonate is then evaporated off to dryness. The residue is taken up with 100 cm³ of an 18% solution of acetic acid in water.

After extraction with ethyl acetate, the organic phase is dried over magnesium sulfate and then evaporated to dryness to obtain, after recrystallization in a toluene/cyclohexane mixture, 2-(1-naphthyl)-2-(methoxycarbonyl)acetonitrile.

Yield: 88% Melting point: 89°-90° C.
Spectral characteristics
Infrared: ν C≡N: 2240 cm⁻¹ ν CO (ester): 1745 cm⁻¹

NMR (CDCl₃): 3.78 ppm; (singlet, 3H); COOCH₃ 5.40 ppm; (singlet, 1H); CH 7.40-8.70 ppm; (unresolved complex, 7H); aromatic H

Stage B:
2-(1-naphthyl)-2-(methoxycarbonyl)ethylamine 0.02 mol of 2-(1-naphthyl)-2-(methoxycarbonyl)acetonitrile is dissolved in 250 cm³ of methanol, and 0.04 mol of cobalt chloride is then added. 0.14 mol of sodium borohydride is added in small portions while cooling, which causes the formation of a black precipitate. The mixture is left stirring for 2 hours at room temperature. It is then slightly acidified by adding 3N hydrochloric acid until the black complex has dissolved, the methanol is thereafter evaporated off and an extraction is carried out with ethyl acetate. The aqueous phase is alkalinized with concentrated ammonia solution. It is then extracted twice with ethyl acetate, the organic phase is dried over magnesium sulfate and taken to dryness, the residue is thereafter taken up in absolute alcohol and gaseous hydrogen chloride is bubbled through. The mixture is taken to dryness and, after recrystallization in acetonitrile, 2-(1-naphthyl)-2-(methoxycarbonyl)ethyl]amine is obtained.

Yield: 42% Melting point (hydrochloride): 217°-219° C.

Spectral characteristics (hydrochloride):
Infrared: ν NH₂: 3300-2500 cm⁻¹ ν CO (ester): 1720 cm⁻¹

NMR (DMSO): 3.00-3.80 ppm; (multiplet, 4H); CH₂+H₂O 3.60 ppm; (singlet, 3H) ; COOCH₃ 5.07 ppm; (doublet, 1H) ; CH 7.30-8.25 ppm; (unresolved complex, 7H) ; aromatic H 8.12 ppm; (signal, 3H); NH₃+Cl−

Stage C:
N-[2-(1-naphthyl)-2-(methoxycarbonyl)ethyl]cyclobutanecarboxamide 0.01 mol of the hydrochloride of the amine obtained in the preceding stage is dissolved in 100 cm³ of a water/chloroform (40:60, vol/vol) mixture, and 0.02 mol of potassium carbonate is then added with magnetic stirring. The reaction mixture is cooled in an ice bath, and 0.01 mol of cyclobutanecarbonyl chloride is then added dropwise and with magnetic stirring. After stirring has been maintained for 30 minutes at room temperature, the chloroform phase is separated, washed with water and dried over calcium chloride, and the chloroform is then evaporated off under vacuum to obtain, after recrystallization of the residue in a toluene/cyclohexane mixture, N-[2-(1-naphthyl)-2-(methoxycarbonyl)ethyl]cyclobutanecarboxamide.

Yield: 79% Melting point: 88°-90° C.
Elemental microanalysis:

|            | % C   | % H  | % N  |
|------------|-------|------|------|
| calculated | 73.28 | 6.79 | 4.49 |
| found      | 73.19 | 6.78 | 4.47 |

Spectral characteristics
Infrared: ν NH: 2240 cm⁻¹ ν CO (ester: 1730 cm⁻¹ ν CO (amide): 1640 cm⁻¹

NMR (CDCl₃): 1.74-2.4 ppm; (unresolved complex, 6H); cyclobutyl CH₂ 2.75-3.10 ppm; (unresolved complex, 1H) ; cyclobutyl CH 3.40-4.10 ppm; (unresolved complex, 2H) ; CH₂ 3.72 ppm; (singlet, 3H); COOCH₃ 4.80 ppm; (doublet of doublet, 1H); CH 5.85 ppm; (signal, 1H); NH 7.3-8.4 ppm; (unresolved complex, 7H); aromatic H

EXAMPLE 12

N-[2-(1-naphthyl)-2-(methoxycarbonyl)ethyl]cyclopropanecarboxamide

Using the procedure described in Example 13, but replacing cyclobutanecarbonyl chloride in stage C by cyclopropanecarbonyl chloride, N-[2-(1-naphthyl)-2-(methoxycarbonyl)ethyl]cyclopropanecarboxamide is obtained. Recrystallization solvent: toluene/cyclohexane Yield: 83% Melting point: 140°-142° C.

EXAMPLES 13 AND 14

Using the procedure described in Example 11, but replacing cyclobutanecarbonyl chloride in stage C by the corresponding acyl halide, the compounds of the following examples are obtained:

EXAMPLE 13

N-[2-(1-naphthyl)-2-(methoxycarbonyl)ethyl]propionamide

EXAMPLE 14

N-[2-(1-naphthyl)-2-(methoxycarbonyl)ethyl]-3-cyclopentylpropionamide

EXAMPLES 15 TO 19

Using the procedure described in Example 11, but replacing 2-(1-naphthyl)acetonitrile in stage A by 2-(7-methoxy-1naphthyl)acetonitrile (EP 447,285) and using the appropriate acyl halides in stage C, the following compounds are obtained:

EXAMPLE 15

N-[2-(7-methoxy-1-naphthyl)-2-(methoxycarbonyl)ethyl]cyclopropanecarboxamide
Recrystallization solvent: toluene/cyclohexane mixture
Yield: 76% Melting point: 95°–96° C.
Elemental microanalysis:

|  | % C | % H | % N |
|---|---|---|---|
| calculated | 69.70 | 6.46 | 4.27 |
| found | 70.05 | 6.53 | 4.32 |

EXAMPLE 16

N-[2-(7-methoxy-1-naphthyl)-2-(methoxycarbonyl)ethyl]cyclobutanecarboxamide

EXAMPLE 17

N-[2-(7-methoxy-1-naphthyl)-2-(methoxycarbonyl)ethyl]trifluoromethanecarboxamide

EXAMPLE 18

N-[2-(7-methoxy-1-naphthyl)-2-(methoxycarbonyl)ethyl]propionamide

EXAMPLE 19

N-[2-(7-methoxy-1-naphthyl)-2-(methoxycarbonyl)ethyl]morpholinoacetamide

EXAMPLE 20

N-[2-(7-methoxy-1-naphthyl)-2-(methoxycarbonyl)ethyl]acetamide

A solution of 0.04 mol of 2-(7-methoxy-1-naphthyl)acetonitrile in 150 cm$^3$ of acetic anhydride in the presence of 5 g of catalyst (Raney nickel) is subjected to a hydrogen pressure of 20.7 bars for 30 hours at a temperature of 60° C. with stirring.

After filtration of the catalyst and evaporation of the solvent under vacuum, the residual oil is taken up with 250 cm$^3$ of ethyl acetate. The organic phase is washed with saturated sodium carbonate solution and then with water. After drying over sodium sulfate, it is evaporated to dryness, and the residue is then recrystallized in a toluene/hexane (2:1) mixture to obtain N-[2-(7-methoxy-1-naphthyl)-2-(methoxycarbonyl)ethyl]acetamide
Yield: 70% Melting point: 118°–120° C.
Spectral characteristics:
Infrared: $\nu$ NH: 3280 cm$^{-1}$ $\nu$ CO (ester): 1730 cm$^{-1}$ $\nu$ CO (amide): 1650 cm$^{-1}$

EXAMPLES 21 TO 23

Using the procedure described in Example 13, but replacing dimethyl carbonate in stage A by diethyl carbonate, the compounds of the following examples are obtained:

EXAMPLE 21

N-[2-(1-naphthyl)-2-(ethoxycarbonyl)ethyl]cyclobutanecarboxamide

EXAMPLE 22

N-[2-(1-naphthyl)-2-(ethoxycarbonyl)ethyl]cyclobutanecarboxamide

EXAMPLE 23

N-[2-(1-naphthyl)-2-(ethoxycarbonyl)ethyl]propionamide

EXAMPLE 24

N-[2-(7-hydroxy-1-naphthyl)ethyl]cyclopropanecarboxamide 13.8 g (5.81×10$^{-2}$ mol) of 2-(7-methoxy-1-naphthyl)ethylamine hydrochloride and 46 cm$^3$ of 47% hydrobromic acid solution are introduced into a 250-cm$^3$ round-bottom flask with a ground neck. The mixture is brought to reflux for 6.5 hours. After cooling, the reaction medium is filtered. The precipitate is washed with water and then with hexane. Recrystallization of the crude product is carried out in an ethyl acetate/hexane mixture to obtain 2-(7-hydroxy-1-naphthyl)ethylamine hydrobromide (yield 80%; melting point: 174°–175° C.).

12.4 g (8.9×10$^{-2}$ mol) of potassium carbonate are then dissolved in 50 cm$^3$ of water in a 500-cm$^3$ conical flask. With good stirring, 12.4 g (4.62×10$^{-2}$ mol) of the 2-(7-hydroxy-1-naphthyl)ethylamine hydrobromide obtained above are added. 200 cm$^3$ of chloroform are added, and a chloroform solution (10 cm$^3$) of 4.95 g (4.64×10$^{-2}$ mol) of cyclopropanecarbonyl chloride is then introduced dropwise. This addition is performed with vigorous stirring. Reaction is complete when no solid remains in suspension. The reaction medium is allowed to settle, the aqueous phase is separated and the chloroform phase is washed with water and then dried over magnesium sulfate. The solvent is evaporated off under reduced pressure. After recrystallization in toluene, N-[2-(7-hydroxy-1-naphthyl)ethyl]cyclopropanecarboxamide is obtained.
Yield: 67% M.p.=140°–141° C.
Spectral characteristics:
Infrared: $\nu$ OH and NH: 3330 cm$^{-1}$ $\nu$ C=C+C—C(cyclopropyl): 3200–3100 cm$^{-1}$ $\nu$ CH: 2900–3000 cm$^{-1}$ $\nu$ CO (amide): 1640 cm$^{-1}$

EXAMPLE 25

N-{2-[7-(cyclohexen-3-yl)oxy-1-naphthyl]ethyl}cyclopropanecarboxamide

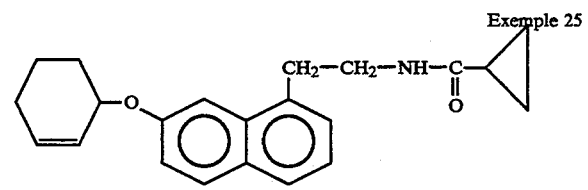

Exemple 25

2.74 g (1.98×10$^{-2}$ mol) of potassium carbonate, 3.4 g (1.33×10$^{-2}$ mol) of N-[2-(7-hydroxy-1-naphthyl)e- thyl]cyclopropanecarboxamide, obtained in Example 24 and dissolved in 20 cm³ of anhydrous acetone, and 3.4 g ($2.1 \times 10^{-2}$ mol) of 3-bromocyclohexene are introduced into a 50-cm³ round-bottom flask with a ground neck. The mixture is heated to reflux for 22 hours. The reaction medium is filtered and the filtrate is evaporated under reduced pressure. Recrystallization of the evaporation residue in ethyl acetate enables purified N-{2-[7-(cyclohexen-3-yl)oxy-1-naphthyl]ethyl}cyclopropanecarboxamide to be obtained.

Yield: 85% M.p.=132°-133° C.

Elemental microanalysis: calculated C % 78.78 H % 7.50 N % 4.18 found C % 78.25 H % 7.48 N % 4.15

Spectral characteristics: Infrared: $\nu$ NH (twisting): 3300 cm⁻¹ $\nu$ C=C+C—C(cyclopropyl): 3020–3150 cm⁻¹ $\nu$ CH: 2900–2960 cm⁻¹ $\nu$ CO (amide): 1640 cm⁻¹ $\nu$ NH (stretching): 1250 cm⁻¹

EXAMPLE 26

N-[2-(7-benzyloxy-1-naphthyl)ethyl]cyclopropanecarboxamide 0.23 gram of sodium is added in small portions and with magnetic stirring into a 150-cm³ round-bottom flask containing 50 cm³ of absolute ethanol.

0.01 mol of N-[2-(7-hydroxy-1-naphthyl)ethyl]cyclopropanecarboxamide (obtained in Example 24) is then added, stirring is continued for 30 min and the mixture is then evaporated to dryness.

The sodium compound obtained is dissolved in 30 cm³ of anhydrous dimethylformamide. With magnetic stirring, 0.011 mol of benzyl bromide is added via a dropping funnel.

The mixture is heated to 90° C. for 4 hours. It is allowed to cool, and the reaction medium is then poured onto ice. The precipitate formed is drained and washed with 1N sodium hydroxide solution and then with water. It is dried and recrystallized to obtain purified N-[2-(7-benzyloxy-1-naphthyl)ethyl]cyclopropanecarboxamide.

Recrystallization solvent: 95° strength alcohol/water mixture

Yield: 66% Melting point: 119°-120° C.

Spectral characteristics:
Infrared: $\nu$ NH: 3280 cm⁻¹ $\nu$ CO: 1625 cm⁻¹

EXAMPLE 27

N-[2-(7-diphenylmethyloxy-1-naphthyl)ethyl]cyclopropanecarboxamide

Using the procedure described in Example 26, but replacing benzyl bromide by (diphenyl)methyl bromide, N-[2-(7-diphenylmethyloxy-1-naphthyl)ethyl]cyclopropanecarboxamide is obtained.

Recrystallization solvent: hexane
Yield: 62% Melting point: 109°-111° C.
Spectral characteristics:
Infrared: $\nu$ NH: 3280 cm⁻¹ $\nu$ CO: 1635 cm⁻¹

EXAMPLE 28

N-[2-(7-cyclohexyloxy-1-naphthyl)ethyl]cyclopropanecarboxamide

An alcoholic solution (35 cm³) of 0.8 g ($2.385 \times 10^{-3}$ mol) of the cyclohexene compound obtained in Example 25 is subjected to a catalytic hydrogenation in the cold state for 15 hours under a hydrogen pressure of 1 bar in the presence of 0.8 g of activated palladium on charcoal. The reaction medium is then filtered and the filtrate is thereafter evaporated under reduced pressure. The evaporation residue is recrystallized in a methanol/water mixture. 0.65 g of purified product, N-[2-(7-cyclohexyloxy-1-naphthyl)ethyl]cyclopropanecarboxamide, is obtained.

Yield: 81%
Recrystallization solvent: methanol/water
Melting point: 153°-155° C.
Spectral characteristics:
Infrared: $\nu$ NH (twisting): 3300 cm⁻¹ $\nu$ C=C+C—C (cyclopropyl): 3020–3150 cm⁻¹ $\nu$ CH: 2900–2960 cm⁻¹ $\nu$ C=O (ether): 2840 cm⁻¹ $\nu$ C=O (amide): 1640 cm⁻¹ $\nu$ NH (stretching): 1250 cm⁻¹

EXAMPLE 29

N-ethyl-N-[2-(1-naphthyl)ethyl]cyclobutanecarboxamide

Stage A: N-ethyl-N-[2-(1-naphthyl)ethyl]amine

A solution composed of 0.03 mol of N-[2-(1-naphthyl)ethyl]amine hydrochloride, 0.03 mol of chloroethane, 0.06 mol of potassium carbonate and 50 cm³ of acetone is prepared.

The mixture is brought to reflux with stirring for 12 hours. After evaporation, the residue is taken up with ether and the ether phase is then exhaustively extracted with 1N hydrochloric acid. The acid phase is alkalinized in the cold state and extracted with ether and the organic phase is dried. After evaporation, N-ethyl-N-[2-(1-naphthyl)ethyl]amine is obtained.

Stage B:
N-ethyl-N-[2-(1-naphthyl)ethyl]cyclobutanecarboxamide

Using the procedure described in Example 1, but replacing N-[2-(1-naphthyl)ethyl]amine by the secondary amine obtained in the preceding stage, N-ethyl-N-[2-(1-naphthyl)ethyl]cyclobutanecarboxamide is obtained.

EXAMPLES 30 TO 32

Using the procedure described in Example 11, but replacing 2-(1-naphthyl)acetonitrile in stage A by 2-(5-methoxy-1-naphthyl)acetonitrile and using the appropriate acyl halides in stage C, the compounds of the following examples are obtained:

EXAMPLE 30

N-[2-(5-methoxy-1-naphthyl)-2-(methoxycarbonyl)ethyl]cyclobutanecarboxamide

EXAMPLE 31

N-[2-(5-methoxy-1-naphthyl)-2-(methoxycarbonyl)ethyl]cyclopropanecarboxamide

EXAMPLE 32

N-[2-(5-methoxy-1-naphthyl)-2-(methoxycarbonyl)ethyl]acetamide

EXAMPLE 33

N-[2-(1-naphthyl)-2-(methoxycarbonyl)ethyl]-N'-propylurea 0.011 mol of propyl isocyanate is added dropwise and with magnetic stirring to a suspension of 0.01 mol of 2-(1-naphthyl)-2-(methoxycarbonyl)ethylamine hydrochloride, obtained in stage B of Example 11, in 5 cm³ of pyridine. The reaction medium is stirred for 1 hour at a temperature of 80° C. and then poured into ice-cold water. The mixture is acidified with 1N hydrochloric acid solution. The precipitate formed is drained, washed with water, dried and then recrystallized in a toluene/cyclohexane mixture.

EXAMPLES 34 TO 36

By replacing propyl isocyanate in Example 33 by the corresponding isocyanate, the compounds of the following examples are obtained:

EXAMPLE 34

N-[2-(1-naphthyl)-2-(methoxycarbonyl)ethyl]-N'-benzylurea

EXAMPLE 35

N-[2-(1-naphthyl)-2-(methoxycarbonyl)ethyl]-N'-cyclobutylurea

EXAMPLE 36

N-[2-(1-naphthyl)-2-(methoxycarbonyl)ethyl]-N'-butylurea

EXAMPLES 37 TO 39

Using the procedures described in the Examples 1 to 3, but replacing 2-(1-naphthyl)acetonitrile in Example 1 by 2-(2-naphthyl)acetonitrile, the compounds of the following examples are obtained:

EXAMPLE 37

N-[2-(2-naphthyl)ethyl]cyclobutanecarboxamide

EXAMPLE 38

N-[2-(2-naphthyl)ethyl]cyclopropanecarboxamide

EXAMPLE 39

N-[2-(2-naphthyl)ethyl]trifluoromethanecarboxamide

EXAMPLE 40

N-[2-(2-naphthyl)-2-(methoxycarbonyl)ethyl]cyclobutanecarboxamide

Using the procedure described in Example 11, but replacing 2-(1-naphthyl)acetonitrile in stage A by 2-(2-naphthyl)acetonitrile, N-[2-(2-naphthyl)-2-(methoxycarbonyl)ethyl]cyclobutanecarboxamide is obtained.

EXAMPLE 41

N-[2-(7-hydroxy-1-naphthyl)ethyl]cyclobutanecarboxamide

Using the procedure described in Example 24, but replacing cyclopropanecarbonyl chloride by cyclobutanecarbonyl chloride, N-[2-(7-hydroxy-1-naphthyl)ethyl]cyclobutanecarboxamide is obtained.

EXAMPLE 42

N-{2-[7-(cyclohexen-3-yl)oxy-1-naphthyl]ethyl}cyclobutanecarboxamide

Using the procedure described in Example 25, but replacing the compound obtained in Example 24 by the compound obtained in Example 41, N-{2-[7-(cyclohexen-3-yl)oxy-1-naphthyl]ethyl}cyclobutanecarboxamide is obtained.

Melting point: 104°–106° C.
Microanalysis:

| % | C | N | H |
|---|---|---|---|
| theoretical | 79.04 | 7.78 | 4.01 |
| calculated | 78.60 | 7.72 | 3.88 |

EXAMPLE 43

N-[2-(7-cyclohexyloxy-1-naphthyl)ethyl]cyclobutanecarboxamide

Using the procedure described in Example 28, but replacing the compound obtained in Example 25 by the compound obtained in Example 42, N-[2-(7-cyclohexyloxy-1-naphthyl)ethyl]cyclobutanecarboxamide is obtained.

Melting point: 116°–118° C.

EXAMPLE 44

N-[2-(7-hydroxy-1-naphthyl)ethyl]acetamide

Using the procedure described in Example 24, but replacing cyclopropanecarbonyl chloride by acetic anhydride, N-[2-(7-hydroxy-1-naphthyl)ethyl]acetamide is obtained.

Melting point: 125°–126° C.

Pharmacological Study

Example A: Study of Acute Toxicity

The acute toxicity was assessed after oral administration to groups of 8 mice (26±2 grams). The animals were observed at regular intervals during the first day and daily during the two weeks following treatment. The $LD_{50}$, bringing about the death of 50% of the animals, was evaluated.

The $LD_{50}$ of the test products is greater than 1000 mg.kg$^{-1}$ for most of the compounds under study, indicating the low toxicity of the compounds of the invention.

Example B: Study of Binding to Melatonin Receptors

The studies of binding of the compounds of the invention to melatonin receptors were carried out according to standard techniques on sheep pars tuberalis cells. The pars tuberalis of the adenohypophysis is, in effect, characterized in mammals by a high density of melatonin receptors (Journal of Neuroendocrinology vol (1), pp 1–4 (1989)).

Protocol

1) Membranes of sheep pars tuberalis are prepared and used as target tissue in saturation experiments to determine its binding affinities and capacities for [$^{125}$I]iodomelatonin.
2) Membranes of sheep pars tuberalis are used as target tissue with the different test compounds in experiments of competitive binding relative to melatonin.

Each experiment is carried out in triplicate, and a series of different concentrations is tested for each compound.

After statistical treatment, the results enable the binding affinities of the test compound to be determined.

Results

It is apparent that the compounds of the invention possess a potent affinity for melatonin receptors, since they bind with a dissociation constant of the order of 10–11M.

Example C: Study of the Melatonin-Antagonist Activity of the Compounds of the Invention The antagonist activity of the compounds of the invention may be measured on sheep pars tuberalis cells stimulated beforehand with forskolin, in which cells melatonin specifically inhibits cyclic AMP synthesis (J. Mol. Endocr. 1989; 3; R5-R8)

Protocol

Sheep pars tuberalis cells in culture are incubated in the presence of forskolin ($10^{-6}$M) and the test compound, alone or in combination with melatonin ($10^{-9}$M).

Assay of cyclic AMP is carried out by a radioimmunological test.

Each experiment is carried out in triplicate, and several concentrations are tested for each compound so as to establish the dose-response curve and to determine the concentration that inhibits the action of melatonin by 50% (or $IC_{50}$).

Results

The Applicant discovered that the compounds of the invention possessed an antagonist activity which was very potent and considerably greater than the known values in the literature. By contrast, in this test, the compounds of Application EP 447,285 are shown to possess an intense melatonin receptor-agonist activity.

Example D: In Vivo Study of the Melatonin-Antagonist Activity of the Compounds of the Invention In the adult male golden hamster maintained in a photoperiod with extended illumination (light/dark cycle: 14 H/10 H; under these conditions, its sexual system is active), if it is injected daily with melatonin at the end of the period of illumination, this hormone is capable of inducing, after 8 weeks, a complete shutdown of the sexual system (atrophy of the gonads).

By altering the ambient temperature, it has been possible to develop this test further, and this atrophy of the gonads can now be obtained in only 4 weeks.

Under these conditions, a compound capable of preventing the effect of melatonin is considered to be a melatonin receptor antagonist.

Protocol

Groups of 12 adult golden hamsters are placed in the situation of a photoperiod with extended illumination (light/dark cycle: 14 hours/10 hours, night from 6 pm to 4 am) at a temperature of 7° C.

At the end of each period of illumination (between 4 pm and 5 pm), each animal is injected
 either with the solvent (solvent control group)
 with melatonin alone (10 micrograms/day, melatonin control group)
 or with the test compound alone (test-compound control group)
 or with the test compound and melatonin.

The animals are sacrificed after 4 weeks and the atrophy of the gonads is measured.

Results

It is apparent that the compounds of the invention possess in vivo a strong melatonin-antagonist power. In contrast, the compounds of Application EP 447,285 are shown in this test to possess a considerable melatonin receptor-agonist activity.

Example E: Study of the Melatonin-Antagonist Activity of the Compounds with Respect to Pigment Aggregation Melatonin is known to participate in regulation of the skin color of amphibians such as Xenopus (*Xenopus laevis*). It causes condensation of the melatonin- containing granules in the melanophores of the dermis (Sugden D. European Journal of Pharmacology, vol. 213, pp: 405-408 (1992)).

The compounds of the invention were tested for their capacity to inhibit the effect of melatonin on Xenopus melanophores.

Protocol (According to the method described in Sugden D. Br. J. Pharmacol. vol. 104, pp 922-927, (1991)).

The neural crest of Xenopus embryos is dissected and the cells are isolated. The melanophores which appear after 2-3 days of culture are rapidly visible among the other cells emanating from the neural crest. The melanophores are cultured in Leibovitz L-15 medium (Gibco) and diluted (1/1) with deionized water containing 10% of fetal calf serum, 200 IU/$cm^3$ of penicillin, 200 $\mu$g/$cm^3$ of streptomycin and 2.5 $\mu$g/$cm^3$ of amphotericin B.

The experiments on the melanophores are carried out between days 7 and 12 of the culture.

The response of the isolated melanophores to melatonin is quantified by measuring the pigmented area using a computer-assisted image analyzer. The test compounds are added to the culture medium 10 to 15 min before the measurement.

Results

It is apparent that the compounds of the invention strongly antagonize the activity of melatonin.

As an example, the compound of Example 1 significantly antagonizes the action of melatonin ($10^{-8}$M) at a concentration of $10^{-7}$M.

EXAMPLE F: Pharmaceutical Composition: Tablets

Tablets containing a 5 mg dose of N-[2-(1-naphthyl)ethyl]cyclobutanecarboxamide.

Preparation formula for 1000 tablets:

| | |
|---|---|
| N-[2-(1-Naphthyl)ethyl]cyclobutanecarboxamide | 5 g |
| Wheat starch | 1.5 g |
| Corn starch | 1.5 g |
| Lactose | 6.5 g |
| Magnesium stearate | 0.2 g |
| Silica | 0.1 g |
| Hydroxypropylcellulose | 0.2 g |

We claim:

1. A compound selected from those of formula (I):

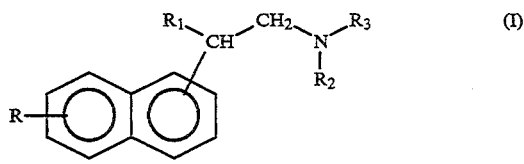

in which:
 R represents hydrogen or a group —O—$R_4$ in which $R_4$ denotes hydrogen or a substituted or unsubstituted group chosen from alkyl, cycloalkyl, cycloalkylalkyl, phenyl, phenylalkyl, and diphenyl,
 $R_1$ represents hydrogen or a group —CO—O—$R_5$ in which $R_5$ denotes hydrogen or substituted or unsubstituted alkyl,
 $R_2$ represents hydrogen or a group —$R'_2$ wherein $R'_2$ represents alkyl or substituted alkyl,
 $R_3$ represents:

a group

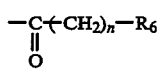

in which n is 0 or 1 to 3 inclusive and $R_6$ represents hydrogen or a radical selected from alkyl, substituted alkyl wherein the substituents are one or more halogen, ($C_1$-$C_4$) alkyl, or ($C_1$-$C_4$) alkoxy, alkene, substituted alkene, cycloalkyl, and substituted cycloalkyl, and a substituted or unsubstituted heterocyclic group chosen from pyrrolidine, piperidine, piperazine, homopiperidine, homopiperazine, morpholine and thiomorpholine;
on the understanding that if:
R represents alkoxy, or
R represents hydrogen and $R_3$ represents a group —CO—$R_8$ in which $R_8$ represents hydrogen, methyl, or a methyl or propyl substituted with one halogen, then $R_1$ cannot be hydrogen,
an optical isomer thereof, or an addition salt thereof with a pharmaceutically-acceptable base,
on the understanding that, except where otherwise specified,
the term "substituted" means that the groups to which it relates may be substituted with one or more radicals chosen from halogen, ($C_1$-$C_4$) alkyl, ($C_1$-$C_4$) alkoxy, phenyl, and phenylalkyl, it being possible for a phenyl ring itself to be substituted with one or more radicals selected from halogen, ($C_1$-$C_4$) alkyl, ($C_1$-$C_4$) alkoxy, hydroxyl, and trifluoromethyl,
the term "alkyl" denotes a alkyl containing 1 to 6 carbon atoms, inclusive, in an unbranched or branched chain,
the term "alkene" denotes a alkene containing 2 to 6 carbon atoms, inclusive, in an unbranched or branched chain,
the term "cycloalkyl" denotes a saturated or unsaturated, mono- or bicyclic group containing 3 to 10 carbon atoms, inclusive.

2. A compound according to claim 1 wherein R represents hydrogen, thereof with a pharmaceutically-acceptable base.

3. A compound according to claim 1 wherein $R_1$ represents a group —CO—O—$R_5$ in which $R_5$ denotes alkyl.

4. A compound according to claim 1 wherein $R_3$ represents a group:

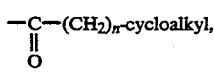

substituted or unsubstituted, with the terms "n" and "cycloalkyl" as defined in claim 1, an optical isomer, and an addition salt thereof with a pharmaceutically-acceptable base.

5. A compound according to claim 1 wherein
R represents hydrogen,
$R_1$ represents a group —CO—O—$R_5$ in which $R_5$ denotes alkyl,
$R_3$ represents a group

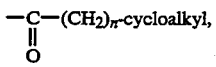

with
the terms "n" and "cycloalkyl" being as defined in claim 1.

6. A compound according to claim 1 which is N-[2-(1naphthyl)ethyl]cyclobutanecarboxamide.

7. A compound according to claim 1 which is N-[2-(1-naphthyl)ethyl]cyclopropanecarboxamide.

8. A compound according to claim 1 which is N-[2-(1-naphthyl)ethyl]trifluoroacetamide.

9. A compound according to claim 1 which is selected from N-[2-(1-naphthyl)-2-(methoxycarbonyl)ethyl]cyclobutanecarboxamide and an optical isomer thereof.

10. A compound according to claim 1 which is selected from N-[2-(1-naphthyl )-2-(methoxycarbonyl)ethyl]cyclopropanecarboxamide and an optical isomer thereof.

11. A compound according to claim 1 which is N-{2-[7-(cyclohexen-3-yl)oxy-1-naphthyl]ethyl}cyclopropane-carboxamide.

12. A compound according to claim 1 which is N-[2-(7-(cyclohexyloxy-1-naphthyl)ethyl]cyclopropanecarboxamide.

13. A compound according to claim 1 which is N-[2-(7-hydroxy-1-naphthyl)ethyl]acetamide.

14. A compound according to claim 1 which is N-[2-(7-benzyloxy-1-naphthyl)ethyl]cyclopropanecarboxamide.

15. A pharmaceutical composition containing as active principle a compound as claimed in claim 1, in combination with one or more pharmaceutically-acceptable excipients or vehicles.

16. A method of treating a mammal afflicted with a disorder linked to abnormal melatonin activity in the body comprising the step of administering to the said mammal an amount of a compound as claimed in claim 1 which is effective for alleviation of said disorder.

17. A compound according to claim 1 which is N-{2-[7-(cyclohexen-3-yl)oxy-1-naphthyl]ethyl}cyclobutanecarboxamide.

18. A compound according to claim 1 which is N-[2-(7-cyclohexyloxy-1-naphthyl)ethyl]cyclobutanecarboxamide.

* * * * *

UNITED STATES PATENT AND TRADEMARK OFFICE
CERTIFICATE OF CORRECTION

PATENT NO. : 5,420,158
DATED : May 30, 1995
INVENTOR(S) : Said Yous, et al

It is certified that error appears in the above-indentified patent and that said Letters Patent is hereby corrected as shown below:

Col. 2, line 66; delete "-".
Col. 8, line 2; change the dash at the end of the line to -- $_2$- --.
Col. 8, line 3; delete "$_2$-" at beginning of line.

Col. 8, line 47; delete "-" from end of line and replace with -- $_2$- -- at end of line.
Col. 8, line 48; delete "$_2$-" from beginning of line.

Col. 8, line 48; delete "6.50" at end of line.
Col. 8, line 49; insert -- 6.50 -- at beginning of line.

Col. 9, line 2; insert -- )_ -- before - (dash) at end of line.
Col. 9, line 3; delete ")" at beginning of line.
Col. 9, line 41; insert -- ) -- before - (dash) at end of line.
Col. 9, line 42; delete ")" at beginning of line.
Col. 9, line 53; insert -- ) -- before - (dash) at end of line.
Col. 9, line 54; delete ")" at beginning of line.
Col. 10, line 42; delete "v" at end of line.

Col. 10, line 43; insert -- v -- at beginning of line.

Col. 11, line 13; insert -- - -- after 1.
Col. 11, line 18; delete "e-" at end of line.

Col. 11, line 19; insert -- e -- at beginning of line.

Col. 11, lines 33, 36, 41, 45 and 49; delete "e" at end of each line leaving the dash.

UNITED STATES PATENT AND TRADEMARK OFFICE
CERTIFICATE OF CORRECTION

PATENT NO. : 5,420,158
DATED : May 30, 1995
INVENTOR(S) : Said Yous, et al

It is certified that error appears in the above-indentified patent and that said Letters Patent is hereby corrected as shown below:

Col. 11, lines 34,37,42,46,50; insert -- e -- at beginning of each line.
Col. 11, line 51; insert -- ) -- before the dash at end of line.
Col. 11, line 52; delete ")" at beginning of line.
Col. 12, line 14; "clobutanecarboxamide" should read -- clopropanecarboxamide --.
Col. 12, line 23; insert -- ) -- before - (dash) at end of line.
Col. 12, line 24; delete ")" at beginning of line.
Col. 12, line 47; delete "space" after ... ene, Col. 12, line 51; delete "(-" at end of line.

Col. 12, line 52; insert -- ( -- at beginning of line.

Col. 12, line 68; delete "e" at end of line leaving the dash.
Col. 13, line 1; insert -- e -- at beginning of line.

Col. 14, line 17; insert -- ) -- before - (dash), at end of line.
Col. 14, line 18; delete ")" at beginning of line.

Col. 14, lines (approx.) 47, 51 and 55; delete "e" at end of each line leaving the dash.

Col. 14, lines (approx.) 48,52 and 56; insert "e" at beginning of each line.

UNITED STATES PATENT AND TRADEMARK OFFICE
CERTIFICATE OF CORRECTION

PATENT NO. : 5,420,158
DATED : May 30, 1995
INVENTOR(S) : Said Yous, et al

It is certified that error appears in the above-indentified patent and that said Letters Patent is hereby corrected as shown below:

Col. 16, line 34; "Melaton" should read -- Melatonin --.

Col. 16, line 62; "10-11M." should read -- $10^{-11}$M. --

Col. 18, line 37 (approx.); delete "e" at end of line leaving the dash.
Col. 18, line 38; insert -- e -- at beginning of line.

Col. 18, line 62; "diphenyl," should read -- diphenylalkyl, --.
Col. 18, line 68; "$R_5$" should read -- $R_3$ --.

Col. 19, line 34; delete "a".
Col. 19, line 37; delete "a".
Col. 19, lines 44 & 45; delete balance of lines after "hydrogen" in line 44.
Col. 19, line 44; "," should read -- . --

Col. 19, line 57 (approx); insert -- being -- before "as"

Col. 19, line 58 (approx); delete "," and rest of line after "1".
Col. 19, line 59 (approx); insert -- . -- after "1".

UNITED STATES PATENT AND TRADEMARK OFFICE
CERTIFICATE OF CORRECTION

PATENT NO. : 5,420,158
DATED : May 30, 1995
INVENTOR(S) : Said Yous, et al

It is certified that error appears in the above-indentified patent and that said Letters Patent is hereby corrected as shown below:

Col. 20, lines 1 and 2; delete lines.

Col. 20, line 17; insert -- - -- after 1.
Col. 20, line 23; delete "e" from end of line leaving the dash.
Col. 20, line 24; insert -- e -- at beginning of line.

Col. 20, line 27 (approx); delete "e" from end of line leaving the dash.
Col. 20, line 28 (approx); insert -- e -- at beginning of line.

Signed and Sealed this

Twenty-ninth Day of August, 1995

BRUCE LEHMAN

Attest:

Attesting Officer

Commissioner of Patents and Trademarks